US010668133B2

(12) United States Patent
Fernandez-Reumann et al.

(10) Patent No.: US 10,668,133 B2
(45) Date of Patent: *Jun. 2, 2020

(54) PROTEIN HYDROLYSATES AS AGENTS TO TREAT SYMPTOMS OF ADDICTION

(71) Applicant: DSM IP ASSETS B.V., Heerlen (NL)

(72) Inventors: Guillen Santiago Eusebio Fernandez-Reumann, Nijmegen (NL); Regina Goralczyk, Basel (CH); Joris Kloek, Delft (NL); Marijn Christoffel Waander Kroes, Nijmegen (NL); Hasan Mohajeri, Basel (CH); Guido Alexander Van Wingen, Nijmegen (NL); Jonas Wittwer, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 103 days.

This patent is subject to a terminal disclaimer.

(21) Appl. No.: 15/377,188

(22) Filed: Dec. 13, 2016

(65) Prior Publication Data
US 2017/0087226 A1 Mar. 30, 2017

Related U.S. Application Data

(63) Continuation of application No. 14/114,466, filed as application No. PCT/EP2012/057638 on Apr. 26, 2012, now abandoned.

(30) Foreign Application Priority Data

Apr. 28, 2011 (EP) .................................... 11164063

(51) Int. Cl.
*A61K 38/47* (2006.01)
*A23L 33/18* (2016.01)
*A23K 20/147* (2016.01)
*A23K 20/189* (2016.01)
*A23L 33/00* (2016.01)
*A61K 9/00* (2006.01)
*A61K 35/57* (2015.01)
*A61K 8/49* (2006.01)
*A61K 8/64* (2006.01)

(52) U.S. Cl.
CPC ............ *A61K 38/47* (2013.01); *A23K 20/147* (2016.05); *A23K 20/189* (2016.05); *A23L 33/18* (2016.08); *A23L 33/30* (2016.08); *A61K 9/0056* (2013.01); *A61K 35/57* (2013.01); *A61K 8/492* (2013.01); *A61K 8/64* (2013.01); *C12Y 302/01017* (2013.01)

(58) Field of Classification Search
CPC ...... A61K 38/47; A61K 35/57; A61K 9/0056; A61K 8/64; A61K 8/492; A23L 33/30; A23L 33/18; A23K 20/189; A23K 20/147; C12Y 302/01017

See application file for complete search history.

(56) References Cited

U.S. PATENT DOCUMENTS

| 9,228,219 B2* | 1/2016 | De Roos ................. C12P 13/22 |
| 9,516,893 B2* | 12/2016 | Gibson ................ A61K 9/0095 |
| 9,629,890 B2 | 4/2017 | Gerhardt |
| 9,993,515 B2* | 6/2018 | De Roos ................. C12P 13/22 |
| 2004/0058866 A1 | 3/2004 | Mallee et al. |
| 2004/0254122 A1 | 12/2004 | Hayes et al. |
| 2005/0089546 A1 | 4/2005 | Wurtman et al. |
| 2006/0257497 A1 | 11/2006 | Bartels-Arntz et al. |
| 2009/0105120 A1 | 4/2009 | Mallee et al. |
| 2009/0270337 A1 | 10/2009 | Van Beckhoven et al. |
| 2010/0087359 A1 | 4/2010 | Bartels-Arntz et al. |
| 2011/0086803 A1 | 4/2011 | De Roos et al. |
| 2011/0110919 A1 | 5/2011 | Gerhardt et al. |
| 2013/0231278 A1 | 9/2013 | De Roos et al. |
| 2013/0296232 A1 | 11/2013 | Gerhardt et al. |
| 2014/0050715 A1 | 2/2014 | Fernandez-Ruemann et al. |
| 2016/0082070 A1 | 3/2016 | De Roos et al. |
| 2017/0087226 A1 | 3/2017 | Fernandez-Reumann |

FOREIGN PATENT DOCUMENTS

| CN | 101535494 A | 9/2009 |
| EP | 1757289 | 2/2007 |
| WO | WO 02/46210 | 6/2002 |
| WO | WO 2004/069265 | 8/2004 |
| WO | WO 2005/049012 | 6/2005 |
| WO | WO 2005/102321 | 11/2005 |
| WO | WO 2006/009448 | 1/2006 |
| WO | WO 2008/052995 | 5/2008 |
| WO | WO 2009/133055 | 11/2009 |

OTHER PUBLICATIONS

O'Connor et. al. The predictive validity of the rat self-administration model for abuse liability. Neuroscience and Behavioral Reviews (Jan. 2011), 35, 912-938. (Year: 2011).*
Hulsken et al, "Food-derived serotonergic modulators: effects on mood and cognition", Nutrition Research Reviews, 2013; 26:223-234.
Khaliq et al, "Relationship of Brain Tryptophan and Serotonin in Improving Cognitive Performance in Rats", Pak. J. Pharm. Sci., 2006; 19:11-15.
Andrews et al, "Is serotonin an upper or a downer? The evolution of the serotonergic system and its role in depression and the antidepressant response", Neuroscience and Biobehavioral Reviews, 2015; 51:164-188.
Polypeptide information downloaded on Apr. 22, 2012 from: ncbi.nlm.nih.gov/protein/BAC06860.1; included as Appendix I to Office Action dated Aug. 15, 2014 in U.S. Appl. No. 13/694,103 (De Roos; Methods of Treatment Using Water-Soluble Tryptophan-Containing Peptides Obtained by the Hydrolysis of Hens Eggs Lysozyme).

(Continued)

*Primary Examiner* — Sean C. Barron
(74) *Attorney, Agent, or Firm* — Nixon & Vanderhye P.C.

(57) ABSTRACT

This invention is directed to the use of a protein hydrolysate, and in particular an egg lysozyme hydrolysate to assist an animal, including a human in overcoming an addition, or by breaking an unwanted habit.

8 Claims, 7 Drawing Sheets

(56) References Cited

OTHER PUBLICATIONS

Vickers, "A Vaccine Against Alzheimer's Disease" Drugs Aging, 2002, 19(7):487-494.
Ferguson, "Depression: Diagnosis and Management for the Primary Care Physician", Prim Care Companion J Clin Psychiatry, Oct. 2000; 2(5):173-178; downloaded Mar. 24, 2014 from ncbi.nlm.nih. gov/pmc/articles/PMC181135; 7 pages total.
International Search Report for PCT/EP2007/061701, dated Jan. 31, 2008.
Mine et al., "Antimicrobial Peptides Released by Enzymatic Hydrolysis of Hen Egg White Lysozyme", Journal of Agricultural and Food Chemistry, vol. 52, (2004), pp. 1088-1094.
Hunter, Howard N., et al., "The Interactions of Antimicrobial Peptides Derived from Lysozyme with Model Membrane Systems", Biochimica Et Biophysica Acta, vol. 1668, (2005), pp. 175-189.
Beulens, Joline W.J. et al., "Alpha-lactalbumin Combined with a Regular Diet Increases Plasma Trp-LNAA Ratio", Physiology & Behaviour, vol. 81, (2004), pp. 585-593.
Hermann, Jacques et al., "Multiple Forms of Duck-Egg-White Lysozyme", European Journal of Biochemistry, vol. 24, (1971), pp. 12-17.
Nishio et al., "Digestion of Protein Substrates by Subtilisin: Immobilization Changes the Pattern of Products", Archives of Biochemistry and Biophysics, vol. 229, (1984), pp. 304-311.
Markus et al, "Evening intake of α-lactalbumin increases plasma tryptophan availability and improves morning alertness and brain measures of attention", Am. J. Clin. Nutr. 81:1026-1033 (2005).
Office Action dated Sep. 1, 2017 mailed in U.S. Appl. No. 14/955,287 (De Roos; Methods of Treatment Using Water-Soluble Tryptophan-Containing Peptides Obtained by the Hydrolysis of Hens Eggs Lysozyme).
International Search Report for PCT/EP2011/066801 dated Feb. 24, 2012.
E.Verschoor et al., "Effects of an Acute Alpha-Lactalbumin Manipulation on Mood and Food Hedonics in High-and Low-Trait Anxiety Individuals" British Journal of Nutrition, vol. 104, No. 4, Aug. 1, 2010 pp. 595-602.
M. Veldhorst et al., "A Breakfast with Alpha-Lactalbumin, Gelatin, or Gelatin + TRP Lowers Energy Intake at Lunch Compared with a Breakfast with Casein, Soy, Whey, or Whey-GMP", Clinical Nutrition, vol. 28, No. 2, Apr. 1, 2009, pp. 0261-5614.
Machine translation of CN101535494A.
Office Action issued in Chinese Patent Application No. 2011-80048202.8 dated Feb. 27, 2014.
C. Markus et al., "The Bovine Protein A-Lactalbumin Increases the Palsma Ratio of Tryptophan to the Other Large Neutral Amino Acids and in Vulnerable Subjects Raises Brain Serotonin Activity, Reduces Cortisol Concentration and Improves Mood Under Stress 1-3", The American Journal of Clinical Nutrition, American Society for Nutrition, vol. 71, Jan. 1, 2000, pp. 1536-1544.
C. Markus et al., "Whey Protein Rich in Alpha-Lactalbumin Increases the Ratio of Plasma Tryptophan to the Sum of the Other Large Neutral Amino Acids and Improves Cognitive Performance in Stress-Vulnerable Subjects", The American Journal of Clinical Nutrition, vol. 75, No. 6, Jun. 1, 2002, whole document.
International Search Report for PCT/EP2012/057638, dated May 31, 2012.
Markus, C.R. et al., "Effect of tryptophan-rich egg protein hydrolysate on brain tryptophan availability, stress and performance", Clinical Nutrition, vol. 29, No. 5, (Oct. 1, 2010), pp. 610-616.
Markus, C.R. et al., "Effect of different tryptophan sources on amino acids availability to the brain and mood in healthy volunteers", Psychopharmacology, vol. 201, No. 1, (Nov. 2008). pp. 107-114.
Van Hierden, Y.M. et al., "Chronic increase of dietary 1-tryptophan decreases gentle feather pecking behaviour", Applied Animal Behaviour Science, vol. 89, No. 1-2, (Nov. 1, 2004), pp. 71-84.
"Lysozyme" (2009 from Internet Archive), from Worthington Enzyme Manual.
Siega-Riz (1998). Trends in breakfast consumption for children in the United States from 1965 to 1991. Am J Clin Nutr., V 67 (suppl), 748S-56S.
Haines (1996). Trends in breakfast consumption of US adults between 1985 and 1991. Am Die Assoc., V 96, p. 464-470.
Smith et al (1986), Dietary Tryptophan Supplements Attenuate Amphetamine Self-Administration in the Rate. Pharmacology Biochemistry and Behavior, V 25(4), p. 849-855.
Rehnquist (2003). Dietary Supplement Labels: Key Elements. Published by DHHS OIA, OEI-01-01120.

* cited by examiner

PROTEIN HYDROLYSATES AS AGENTS TO TREAT SYMPTOMS OF ADDICTION

This application is a continuation of U.S. application Ser. No. 14/114,466 (pending), filed Oct. 28, 2013 (published as US 2014-0050715 A1), which is a U.S. national phase of International Application No. PCT/EP2012/057638, filed 26 Apr. 2012, which designated the U.S. and claims priority to EP Application No. 11164063.7, filed 28 Apr. 2011, the entire contents of each of which are hereby incorporated by reference.

BRIEF DESCRIPTION OF THE INVENTION

This invention is directed to the use of a protein hydrolysate, and in particular an egg lysozyme hydrolysate to assist an animal, including a human in overcoming an addiction, or by breaking an unwanted habit. The invention also includes methods of marketing such a product to consumers by informing the consumer of the addiction-assisting properties of egg lysozyme hydrolysate compositions.

BACKGROUND OF THE INVENTION

Addiction to a physical or emotional stimulus is an ever-increasing problem in today's society. Addictions are notoriously difficult for an individual to overcome, and may involve more than mere determination and will power on behalf of the individual wishing to change their behavior. Alternatively, many people have habits which they would like to break, but have difficulty doing so.

A number of pharmaceutical/psychological strategies are known which aid a person attempting to break an addiction. Examples include use of a nicotine supplement to help a smoker, use of methodone for heroin addicts, use of naloxone for alcoholics, and/or use of various therapies/support groups for those wishing to change a behavior. As evidenced by the high rate of failures and/or reversions to the addictions, however, all these therapies could be improved.

There is even less help available for people who wish to rid themselves of bad habits, which do not rise to the level of clinical addictions, but nonetheless are undesirable behaviors. For these people, pharmaceutical aids may not be warranted, either from a risk standpoint, a financial standpoint, or such aids may not even exist.

WO 2008/052995 (DSM) and Kloek et al 2011 *Agro-FOOD Industry Hi-Tech* 22(1): 27-29 both describe a hydrolyzed lysozyme composition made from lysozyme found in hen's eggs. It contains at least 50%, and preferably at least 75% small peptides which have a molecular weight below 500 Da. This hydrolysate is also characterized in that the ratio of Tryptophan to Large Neutral Amino Acids (the sum of tyrosine, phenylalanine, leucine, isoleucine and valine), often designated the "Trp/LNAA ratio", is at least 0.15, and preferably between 0.15 to 0.20 It was found that by eating this hydrolysate, a person's Trp/LNAA ratio in the blood serum can increase rapidly, and this can have a number of beneficial effects, including a positive influence on sleep quality, a positive effect on a person's mood, increase cognition (i.e. problem solving, learning, memory and language ability), alertness/vigilance, decreased anxiety, and increased libido. However, this is silent as to use as an agent which can help overcome addictions or to dehabituate.

WO2005/049012 (SHS International) discloses that a daily dose of 1-7 grams of tryptophan (14-100 mg/kg body weight) may be used to promote and/or maintain abstinence from additive substances, or from reward-mediated behaviors, and in particular alcohol. The tryptophan is in the form of either free tryptophan or tryptophan salts, and preferably avoids the provision of other LNAAs (large neutral amino acids, i.e. phenylalanine, tyrosine, valine, isoleucine, methionine and histidine). In preferred embodiments, the Trp is delivered with a carbohydrate.

It would be desirable to have a natural food supplement which can function by helping a person lessen or end an addiction or habituation, and which could be used at lower dosages that what has been used in the past, since pure tryptophan can have side effects like drowsiness.

DETAILED DESCRIPTION OF THE INVENTION

It has been found in accordance with this invention, that a hydrolyzed lysozyme composition characterized by a Trp/LNAA ratio between 0.15 and 0.20, and which provides a daily dose of up to 800 mg Trp can rapidly act on the portions of the brain which is involved in reward by reducing brain functions during reward anticipation. Thus, the hydrolyzed lysozyme composition can be used to help an individual overcome an undesired habit or addiction by lessening the reward which is derived from indulging in the behavior.

Thus, one aspect of this invention is a hydrolyzed lysozyme composition which is useful for assisting an animal, including a human in refraining from an undesired behavior, and/or resisting from indulging in an addictive behavior, or a reward-seeking behavior. In some embodiments the animal is a human.

In preferred embodiments the hydrolyzed lysozyme composition does not contain any free Trp; and the Trp is present in peptide-form only.

Another aspect of the invention is a method of assisting an animal, including a human, in refraining from an undesired behavior, and/or resisting from indulging in an addictive behavior or a reward-based behavior comprising a) administering a hydrolyzed lysozyme composition which provides a daily dose of up to 800 mg Trp, and b) noticing or appreciating a lessening of the occurrence of the behavior, or abstinence from the behavior.

Another aspect of this invention is a method of doing business comprising marketing a hydrolyzed lysozyme composition for sale to a consumer wherein the hydrolyzed lysozyme composition provides a daily dose of up to 800 mg Trp, comprising providing a kit, wherein the kit comprises
a) a hydrolyzed lysozyme composition; and
b) information concerning the benefits that the composition has in assisting an animal, including a human, in refraining from an undesired behavior, and/or resisting from indulging in an undesired behavior. The use may also be in combination with an established therapy (pharmocological and/or psychological). The information may be provided by supplying information on the packaging, providing a package insert, by a displaying the information in proximity to the composition, or through other separate advertising media which is not in physical proximity to the product, i.e. by television, radio, internet, billboards, or other known advertising methods. Alternatively, the information may be in the form of personal communication, such as that occurring in a counseling or group help session.

DEFINITIONS

Figure 1:
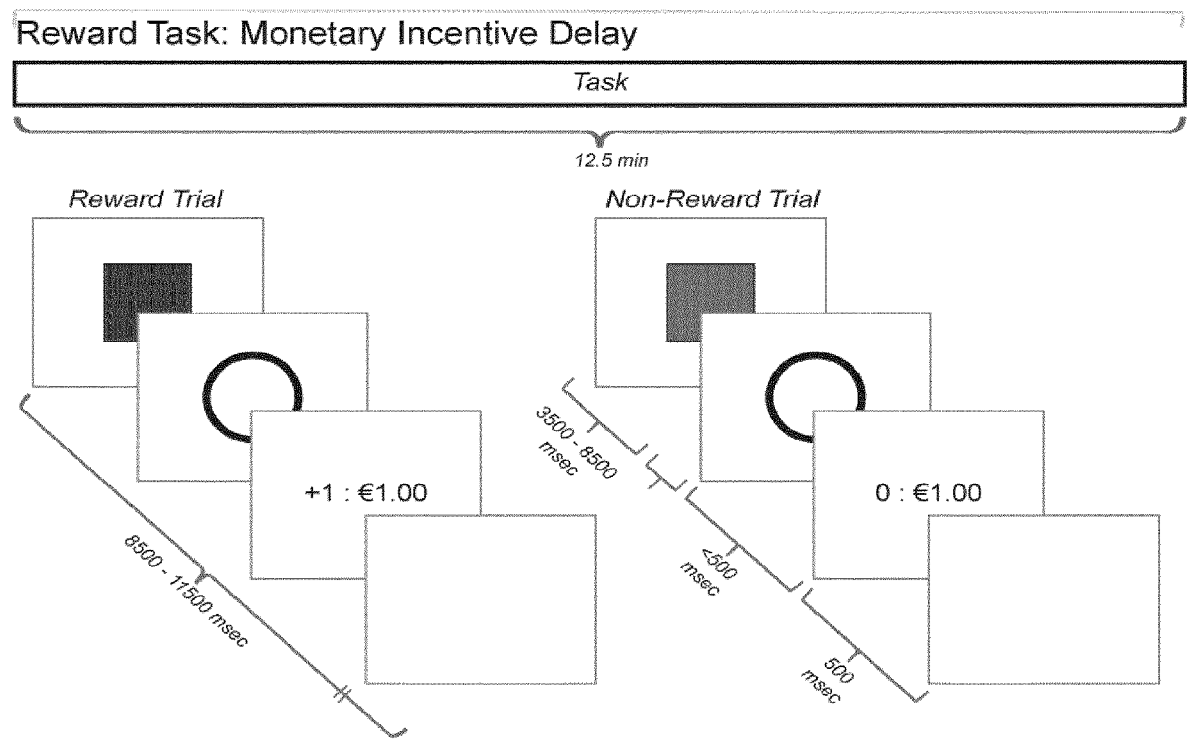
FIG. 1 is a diagram of the "Reward Task". While Blood Oxygen Level Dependent (BOLD) functional Magnetic Resonance Imaging (fMRI) was acquired, reward and non-reward trials were randomly presented. Subjects were cued with a red (reward) or green (non-reward) square of the type of trial. Following a flexible delay a target appeared (black circle). Subjects were asked to make a speeded button press at the moment of target appearance. If the response was on time, the subject earned a monetary reward for which they received feedback. However, rewards could only be obtained when a Reward-Cue had been presented, as was instructed to subjects prior to task.

The following definitions apply throughout the specification and claims.

The "hydrolyzed lysozyme" of this invention is preferably a hen egg lysozyme, and more preferably a hen lysozyme as described in WO2008/052995 (US 2013/0231278). In preferred embodiments it is a mixture of at least two water-soluble tryptophan-containing peptides, having a Trp/LNAA ratio of more than 0.15, and preferably between 0.15 and 0.20. It can be produced according to the process described in US 2013/0231278 A1, which is hereby incorporated by reference, which includes the step of hydrolyzing lysozyme to a degree of hydrolysis of between 5 and 45, preferably between 10 and 40, and optionally removing part of the arginine or lysine containing peptides. In some embodiments, the molecular mass of the peptides produced is less than 500 D. One such hydrolyzed lysozyme is commercially available from DSM Nutritional Products, Basel, Switzerland under the trademark LumiVida®. The hydrolyzed lysozyme may be mixed with food and/or pharmaceutical and/or nutraceutical carriers.

The terms "addictive" or "undesired" or "reward-seeking" behaviors is intended to refer to behaviors which are considered (either by the individual or by society) to be dangerous, potentially harmful or otherwise undesirable, or which are intended to be refrained from, yet the individual finds them difficult to refrain from. Examples of such behaviors in humans include:

smoking,
alcohol abuse,
gambling,
drug abuse (such as cocaine, heroin, prescription painkillers and the like)
compulsive behaviors (including behaviors typically associated with obsessive/compulsive disorder such as excessive hand-washing, repeatedly re-tracing one's steps, or getting out of bed repeatedly to check on whether the door has been locked)
other uncontrollable behaviors such as compulsive shopping, eating, hoarding, sexual behaviors, kleptomania, pyromania, etc)
the potentially harmful risky behaviors of the thrill seeking "adrenaline junkie".
Craving, obsessive eating disorder
Cutting or other self-harm syndrome
Improper sexual behavior/voyeurism Each of these behaviors has a common element: each stimulates a reward/pleasure center in the brain, and the promise of the pleasure surrounding the activity can override the individual's ability to refrain from the activity, even if the individual ultimately wishes to do so.

"Refrain" or "Prevention" of the behavior is not intended to encompass only the situation where the behavior is never performed again; rather it may also encompasses a lessening of the occurrence of the behavior, a lessening of the severity of the behavior, or a general improvement of the condition associated with the behavior. For example, the number of cigarettes smoked may be reduced, the amount of time spent on compulsive behaviors is lessened, or the amount of drug abuse is lessened.

The hydrolyzed lysozyme composition may be used alone, or in combination with another therapy. For example, for someone wishing to give up cigarette smoking, the lysozyme composition may be used in combination with anti-smoking aids, such as nicotine patches or gums, anti-smoking counseling, or the like. For heroin addicts, the lysozyme hydrolysate may be used in combination with methadone, or other similarly-based treatments. For alcoholics, it may be used in combination with naloxone and/or group therapies or similar treatments. Thus, another aspect of this invention is the use of a hydrolyzed lysozyme as an adjunctive treatment or supportive accompanying diet during dehabituation programs, or to assist dehabituation processes.

The invention also has a veterinary application. Animals, particularly those under stress, can develop so-called stereotypic behaviors. Examples of these include the pacing observed in zoo animals (such as polar bears), repeated swallowing of air (observed in horses), uncontrolled eating (observed in dogs), or uncontrolled grooming/licking Thus another aspect of this invention is the use of a lysozyme hydrolysate as part of an animal feed for the purpose of controlling unwanted stereotypic or pathological behaviors in an animal. A further aspect of this invention is a method of controlling unwanted stereotypic or pathological behaviors in an animal comprising administering an effective amount of lysozyme hydrolysate to the animal and observing improved behaviors. Animals which can benefit include: farm animals, companion animals, racing animals, working animals and pets.

Dosages

The lysozyme hydorlysate may be in any form suitable for oral administration such as an additive to or supplement for feed or food, food or feed premix, tablets, pills granules, dragees, capsules, or effervescent formulations such as powers or tablets. It may also be in a liquid form such as a solution, emulsion or suspensions as in beverages, pastes or oily suspensions. Controlled or delayed release formulations may also form part of this invention. Furthermore a multi-vitamin/mineral supplement may be added to the nutraceutical composition.

For human use, one recommended amount is 0.25-5 grams per day hydrolyzed lysozyme (based on a 60 kg body weight), but may be higher, such as up to 12 or 15 g/day. Alternatively, the amount of hydrolyzed enzyme should provide the equivalent of approximately at least 500 mg Trp, preferably 500-900 mg Trp; preferably 500-800 mg Trp, and more preferably at least 800 mg Trp. Doses higher than 800 mg Trp may also be used, but are not generally preferred.

For animals, this amount can be adjusted according to the animal's weight.

In a human trial detailed in the Examples, we found that the consumption of the hydrolyzed lysozyme composition resulted in large increases in Trp/LNAA ratio which affected neural processing of reward. More specifically, hydrolyzed lysozyme composition consumption reduced responses in the dorsal caudate nucleus during reward anticipation.

The reward anticipation task was successful in probing neural circuits previously implicated in reward anticipation in the context of instrumental responses. These regions included the striatum, cingulate cortex, supplementary motor areas, and middle frontal gyrus.

Hydrolyzed lysozyme composition consumption led to a decrease in reward related responses in the dorsal caudate nucleus. Whereas the ventral striatum has been implicated in motivation and the putamen in sensorimotor implementation (stimulus-response coupling), the caudate nucleus has been associated with higher order cognitive processes. More specifically, the dorsal caudate has been associated with active maintenance of goal representation in working memory, possibly via connections with the dorsolateral prefrontal cortex. The ventral aspects of the striatum receives projections from the medial prefrontal cortex (PFC) and orbitofrontal cortex, and the motor cortex projects to dorsolateral putamen with a decreasing projection gradient toward the dorsomedial striatum. This would allow the dorsal caudate to integrate initial emotional responses with cognitive information, and motor outputs. Thus the hydrolyzed lysozyme composition reduced reward related activity in areas implicated in the integration of reward and punishment signals with higher order cognitive information and motor outputs.

While not wishing to be bound by theory, these findings may be due to an increased tonic brain serotonin levels reflecting an overall negative situation. Reward anticipation related signals are down scaled relative to this more negative overall situation, reflected in reduced reward anticipation responses in this task. The dorsal caudate nucleus appears optimally situated to process these integrated signals.

In support of this suggestion, the dorsal striatum has been associated with the monitoring of value over long delays, a process improved by higher serotonin levels, and reflected in plasma Trp levels. (Trp is the precursor of serotonin in the brain). Thus, reduced dorsal caudate signals by increased serotonin levels may echo better maintenance of goals over longer periods of time, and less impulsive switching. Decreased dorsal caudate responses to reward anticipation following increased serotonin would suggest that the caudate integrates average situational negativity (carried by a tonic serotonin signal) with reward signals (phasic dopamine signals) according to which the latter are weight as less rewarding. This implies that the caudate integrates phasic reward and punishment signals with average reward and punishment signals.

In resonance with this idea, the dorsal striatum has been reported to respond to both positive and negative outcomes and responds differentially to reward and punishment relative to the motivational state of a subject, suggesting that the caudate reflects weighted responses. Considering the gradient in serotonin projections in the striatum and the overlap with DA projections in the dorsal striatum, the dorsal caudate would be suited to integrate weighted reward and punishment signals.

We suggest that increased Trp results in increased serotonin levels signaling a negative situation. Reward signals are scaled down relative to this more negative situation. This results in reduced reward related signals in the reward anticipation task leading to a decrease in dorsal caudate activity which integrates this signal with motor output. On a behavioral level this may lead to greater inhibition of impulsive reward seeking and negative thoughts, and reduced responsiveness to aversive events or agitation. In this light it is interesting to note that impulsive reward seeking (craving) has been associated with hyperactive ventral striatum responses in dependency disorders and that caudate hyperactivity is associated with obsessive compulsive disorders, which is reduced by Selective Serotonin Reuptake Inhibitors (SSRI) treatment. Finally, anhedonia, a key symptom of major depression disorder, has been suggested to reflect an inability to sustain positive affect over time, analogue to an inability to inhibit negative thoughts and that caudate volume is correlated with scores on the Becks depression scale.

The following non-limiting Examples are presented to illustrate the invention.

Example 1

Human Clinical Trial

Subjects

Thirty-two healthy young women (age-range: 18-39 yr, mean: 22.387, s.e.m.: 0.701) with normal- or corrected-to-normal vision, and normal uncorrected hearing, were included in the study. All subjects gave informed consent, were free of neurological or psychiatric history, right-handed, used oral hormonal contraceptives, and were tested in the second week of their menstrual cycle. Subjects were free of Magnetic Resonance Imaging (MRI)-contraindications, were not currently pregnant, breastfeeding, planning pregnancy, had not given birth within the last year, or experienced menopausal symptoms. Subjects had no history of prescribed medication within the month prior to study, or over-the-counter medication or cannabis use in the two months prior to study, with the exception of oral contraceptives and paracetamol, and were not recipients of investigational products as part of research studies in the three months prior to initial dose in this study. Subjects did not donate blood in the two months prior to initial study dose. Subjects did not consume more than 10 cigarettes or 3 units of alcohol daily. Subjects tested negative on drug and alcohol screenings. The study was approved by the institutional ethics committee (CMO Regio Arnhem-Nijmegen, The Netherlands).

TABLE 1

Screening characteristics of subjects

| Measure | Mean | SD | Min | Max |
| --- | --- | --- | --- | --- |
| Age (years) | 22.387 | 3.955 | 18 | 39 |
| Heart Rate (units) | 71.452 | 11.384 | 50 | 100 |
| Systolic blood pressure (units) | 118.903 | 12.726 | 92 | 139 |
| Diastolic blood pressure (units) | 70.548 | 8.012 | 60 | 91 |
| Height (cm) | 169.984 | 7.646 | 158 | 185 |
| Weight (Kg) | 68.148 | 8.258 | 53.3 | 83.5 |
| Body Mass Index (units) | 23.531 | 1.789 | 20.24 | 27.11 |

Food Product Consumption

Subjects consumed drinks (300 ml) containing an equal amount of basis protein, but differential tryptophan (Trp) and Large Neutral Amino Acids ("LNAA"), (Valine, Isoleucine, Leucine, Tyrosine, and Phenylalanine) concentrations. The Control Product contained 20 g casein protein hydrolysate with 0.4 g Trp and 10 g LNAA. The Test Product (LumiVida®; DSM Nutritional Products, Kaiseraugst, Switzerland) contained a hydrolyzed enzymatic digest of egg white with 0.8 g TRP and 4 g LNAA (12 g LumiVida®). A sweetener (0.10 g acesulfame) was added to make both formulations more palatable.

Reward Anticipation

The reward anticipation task (FIG. 1) is a modified version of the monetary incentive delay (MID) task in which cues are presented that either signal trials that are potentially rewarding or non-rewarding.

This task consists of 25 potentially rewarding trials, 25 non-rewarding trials and 25 periods of low-level fixation with a mean duration equal to trials. In total, trials last between 8.5 and 11.5 s (mean 10 s). Thus, the total duration of the task is 12.5 min. At the beginning of each trial, a cue (cue duration: 3.5-8.5 s; mean: 6 s) is presented signaling a potentially Rewarding (red square) or Non-Rewarding (green square) trial. Following this cue, a target (white circle) is presented to which subjects have to respond as fast as possible (by pressing a button) irrespective of the cue type. When the button is pressed within the presentation time of the circle, the target remains on the screen, thus providing the participant with feedback that the target is hit. Otherwise, it disappears. When the target is hit on a Reward trial, subjects earn one euro. After disappearance of the target (duration: 1.2-5.3 s; mean 3.25 s), short feedback is provided (500 ms) of the current cumulative gain. To ascertain that reward outcome is similar across participants and sessions, the target duration is variable (150-500 ms) and shortened with 20 ms for the subsequent trial when the previous target is hit. The target duration was lengthened with 10 ms for the subsequent trial when the previous target is missed. This procedure results in a hit rate of ±33% on average, ensuring that all participants win approximately the same amount of money (between 8 and 11 Euros).

Functional MRI (fMRI) DATA fMRI Sequences:

MR data was acquired on a 1.5 T MR scanner (Avanto, Siemens, Medical, Erlangen, Germany) equipped with 8-channel transmit-receiver head coil. The manufacturer's automatic 3D-shimming procedure was performed at the beginning of each experiment. Subjects were placed in a light head restraint within the scanner to limit head movements during acquisition.

Resting State:

Resting state images were acquired using single-shot gradient echo-planar imaging (EPI) with each of 266 images consisting of 39 axial slices (3.0 mm, 17% gap, TR=1.87 s, TE=35 ms, flip angle $\alpha=80°$, Field of View (FOV)=224×224 $mm^2$, Matrix size=64×64.

fMRI Acquisition:

Functional images were acquired with single-shot gradient echo-planar imaging (EPI) sensitive to the blood-oxygenation level dependent (BOLD) response using the following parameters: 32 oblique transverse slices, slice thickness=3.5 mm, matrix size 64×64, fat suppression inter-slice gap=10%, repetition time (TR)=2.34 s, flip angle $\alpha=90°$, echo time (TE)=35 ms (FOV)=212×212 $mm^2$, matrix size 64×64, fat suppression.

Structural Scan

A 3D magnetization-prepared rapid gradient echo (MPRAGE) image was acquired for normalization procedures using the following parameters: TR=2250 ms, TE=3.95 ms, 176 contiguous 1 mm slices, FOV=256×256 $mm^2$, matrix=256×256.

Analysis:

Preprocessing:

fMRI data were processed and analyzed using the statistical software package SPM5 (Wellcome Trust Centre for Neuroimaging, London, UK; http[colon][slash][slash]www[dot]fil[dot]ion[dot]ucl[dot]ac[dot]uk[slash]spm). The first 5 EPI volumes were discarded to allow for T1 equilibration. The remaining functional images from each subject were realigned using rigid-body transformation to correct for head movements to the mean functional image using $2^{nd}$-degree B-spline interpolation and co registered to the anatomical T1-weighted MR image using a normalized mutual information function. Next, images were slice-time corrected to the mean slice. Subsequently, images were spatially normalized into a common stereotactic space (MNI 152 T1-template) and resampled to 2×2×2-$mm^2$ isotropic voxels using trilinear interpolation. Finally, spatial smoothing was applied with an isotropic 30 Gaussian kernel of 8 mm full-width half-maximum.

General Statistics:

The data were modeled voxel-wise, using a general linear model. Trial-specific effects were modeled by trains of stick-or boxcar functions and convolved with the canonical hemodynamic response basis function of SPM5. Additionally, realignment parameters were included to model potential movement artifacts. The data were high-pass filtered (cut-off 128 s) to remove low-frequency signal drifts, and a first-order autoregressive model was used to model the remaining serial correlations. Contrast images of from testing parameter estimates encoding condition-specific effects were created for each subject. The single-subject contrast images were entered into voxel-wise one-sample t-tests to assess main effects of task, and paired-samples t-tests to assess task by drug interactions, implemented in a second-level random effects analysis. We report regions that survive cluster-level correction for multiple-comparisons (family-wise error, FWE) across the whole brain at p<0.05 using an initial height threshold of p<0.001, unless otherwise indicated.

Resting State Analysis:

Significant task by drug interaction were followed up by seed-region analysis to assess covariance of brain region specific activity with a source region. For each subject, the time series from the source region were extracted (the first Eigen variate from the time series of all voxels) and entered together with the realignment parameters as regressors into the first-level model. Averaged time-courses for white-matter and cerebrospinal fluid were added to the first-level models to correct for these compartment signals. Further analysis followed the same method as described above.

Trp/LNAA Covariate Testing:

Finally, to assess whether the product-induced changes in Trp/LNAA ratio predicted neural activity, voxel-wise regression analyses were performed between the product-induced changes in neural activity and the relative Trp/LNAA ratio changes from time-point 1 (baseline) to time-point 2 (90 min after study compound intake), as well as the relative Trp/LNAA ratio changes from time-point 2 (90 min after study compound intake) to time-point 3 (after fMRI tasks).

Task Specific Model Definitions

Reward Anticipation Task:

Two separate regressors were created which modeled the onsets and duration of the reward predicting, and non-reward predicting cues.

Trp/LNAA Analysis:

Blood samples were collected in duplicates of 5 ml vacutainer tubes containing sodium heparin and centrifuged at 1550 g for 5 min at 4° C. The supernatant lithium heparin plasma (750 up was mixed with 120 μl sulfasalicyl acid in duplo and stored at −80° C. until analysis. Plasma amino acid analysis was conducted with high-pressure liquid chromatography (HPLC), making use of a 2- to 3-μm Bischof Spherisorb ODS II column. The plasma tryptophan ratio was calculated by dividing the plasma tryptophan concentration (in μmol/L) by the sum of the other large amino acids, i.e. valine, isoleucine, leucine, tyrosine, and phenylalanine, and averaging over the two samples.

Procedure

Figure 2:
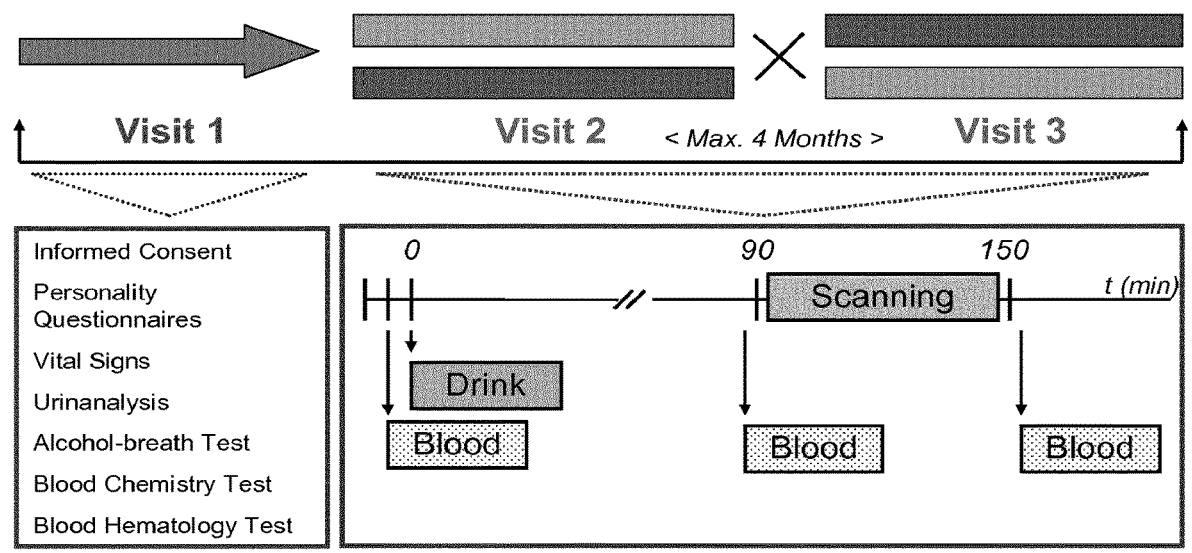
FIG. 2 Study Flow. The study was conducted over 3 visits. During Visit 1 subjects were screened. Next, subjects were tested in a double-blind placebo controlled study on Visit 2 and Visit 3. During Visit 2 and Visit 3, mood questionnaires were administered and blood was sampled for Trp/LNAA determination at three time-points. T1: prior to consumption of either the Test-product or Control product; T2: 90 minutes after consumption just prior to fMRI scanning, T3: post-scanning 150 minutes after consumption.

Visit 1: Screening:

Subjects signed an informed consent form upon which they filled out a demographics and medical history questionnaire (FIG. 2). Vital signs (Heart-rate, blood pressure, body height, body weight, and in-ear temperature were measured). A urine sample was obtained, followed by dipstick urinalysis for pH, leucocytes, nitrite, protein, glucose, ketones, urobilinogen, bilirubin, and erythrocytes/hemoglobin, pregnancy and drug tests opiates, methamphetamines, amphetamines, benzodiazepines, canabinoids, cocaine). An alcohol breath test was administered. A blood sample was obtained for chemistry (3 ml; Albumin, Alkaline phosphatase, Bilirubin, Calcium, Creatine, Gamma-Glutamyl transferase, Inorganic phosphorus, Lactate Dehydrogenase, Potassium, Protein, S-aline aminotransferase, S-aspartate aminotransferase, Sodium, Triglycerides, Urea), haematology (3 ml; erythrocyte sedimentation rate; hematocrit, heamoglobin, thrombocytes, red blood cell count, white blood cell count), deposition (2.4 ml), and glucose (2 ml) analysis. When the subject met all inclusion criteria and none of the exclusion criteria they were randomly assigned to an order of drug administration in a double blind cross-over paradigm.

Visit 2 and 3:

Subjects had a light breakfast free of dairy products or caffeine. Number of days since last menstruation was documented and vital signs were measured. Then, at time-point 1 (T1) a blood sample for Trp/LNAA determination was obtained (2×6 ml). Subsequently, the Test- or Control-product was consumed. Thawing of samples took place in a fridge over night before the start of the study. Thawed samples were consumed within 4 hrs after thawing. Samples were consumed cold. After 90 minutes, at time-point 2 (T2), another blood sample for Trp/LNAA determination obtained (2×6 ml). Next, subjects entered the MR scanner and the Reward anticipation task was conducted. Upon exiting the scanner, at time-point 3 (T3 at about 150 minutes after Product consumption), a blood sample for Trp/LNAA determination was obtained (2×6 ml). Visit 3 followed the same procedure with the exception that the other drug/placebo was consumed and no structural T1-weighted scan was obtained. Following completion of the study subjects were debriefed on the aims and details of the study.

Results

Figure 3:
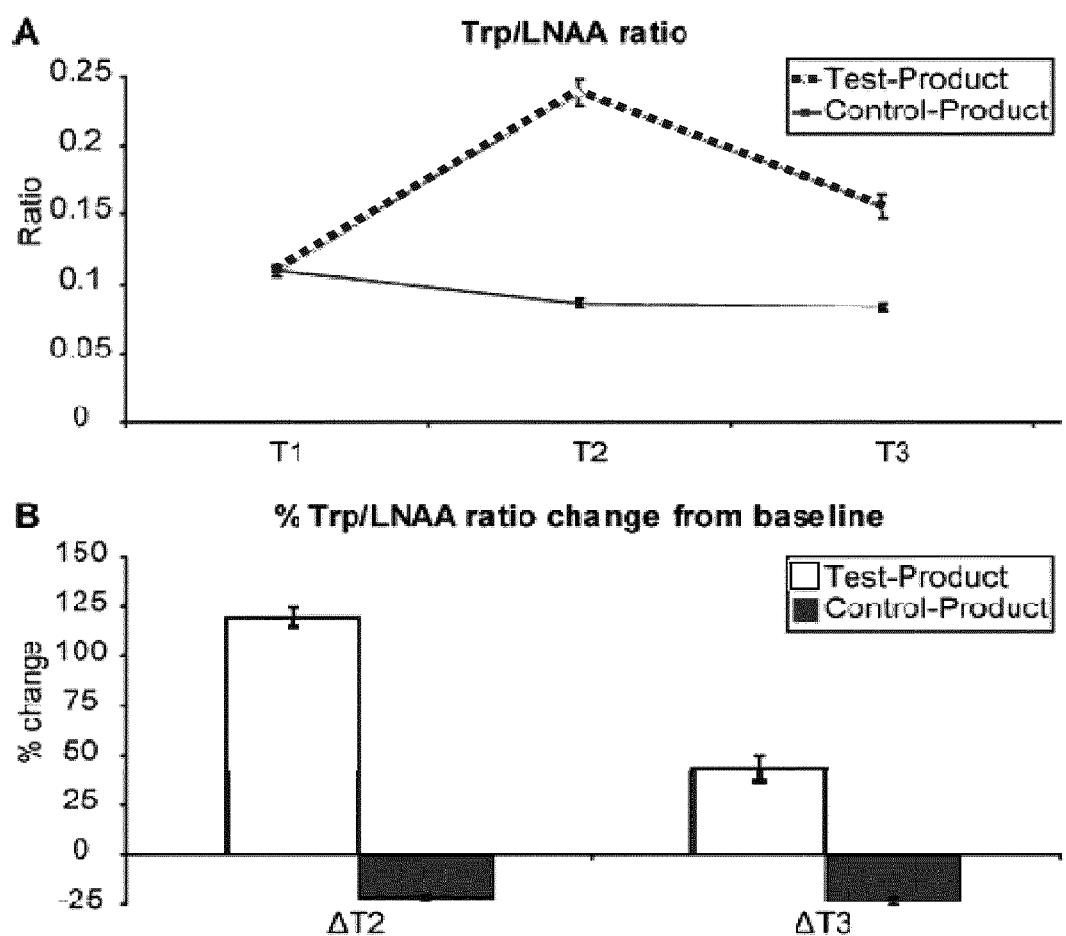
FIG. 3 shows Trp/LNAA plasma results. A: Following Test-Product (hydrolyzed lysozyme) consumption, the Trp/LNAA ratio is more than twofold increased. B: Trp/LNAA ratio change from time-point 1 (baseline) at time point 2 (90 minutes after consumption of products) (Δ2) and time point 3 (post scanning; 150 minutes after consumption of the products) (Δ3).

Trp/LNAA:

For each subject the two measures of Trp/LNAA ratio for each time-point (T1: prior to supplementation; T2: pre-scan, approximately 90 minutes after supplementation; T3: post-scan, approximately 150 minutes after supplementation) were averaged (FIG. 3). A Product (Test-Product, Control-Product) repeated measures ANOVA corrected for Order of Supplementation (Visit 1, Visit 2) on T1 baseline measures did not reveal any main effects (FIG. 3A). As such individual measures at T2 and T3 were divided by the measure at T1, and expressed as a percentage difference from baseline (FIG. 3B).

A Product (Test-Product, Control-Product)×Time (ΔT2, ΔT3) 2×2 repeated measure ANOVA revealed a main effect of Product ($F_{1,29}$=337.350, P<0.001), a main effect of time ($F_{1,29}$=240.593, P<0.001), and an interaction effect of Product×Time ($F_{1,29}$=257.017, P<0.001). Paired T-tests reveal a Trp/LNAA ratio increase following Test-Product consumption relative Control-Product consumption at both ΔT2 (t(29)=26.031, P<0.001 (two-tailed); Test-Product Mean: 119.723, s.e.m.: 4.667, Control-Product Mean: −21.148, s.e.m.: 1.586) and ΔT3 (t(29)=9.429, P<0.001 (two-tailed); Test-Product Mean: 43.837, s.e.m.: 6.07, Control-Product Mean: −23.124, s.e.m.: 1.998), and a significant difference between T2 and T3 following Test-Product consumption (t(29)=16.484, P<0.001 (two-tailed)).

Consumption of the Test-Product caused more than 2-fold increases in Trp/LNAA plasma levels. Although individual variance exists in the amount of change induced by the Test-Product, the increase is highly consistent across subjects.

Behavior

Figure 4:
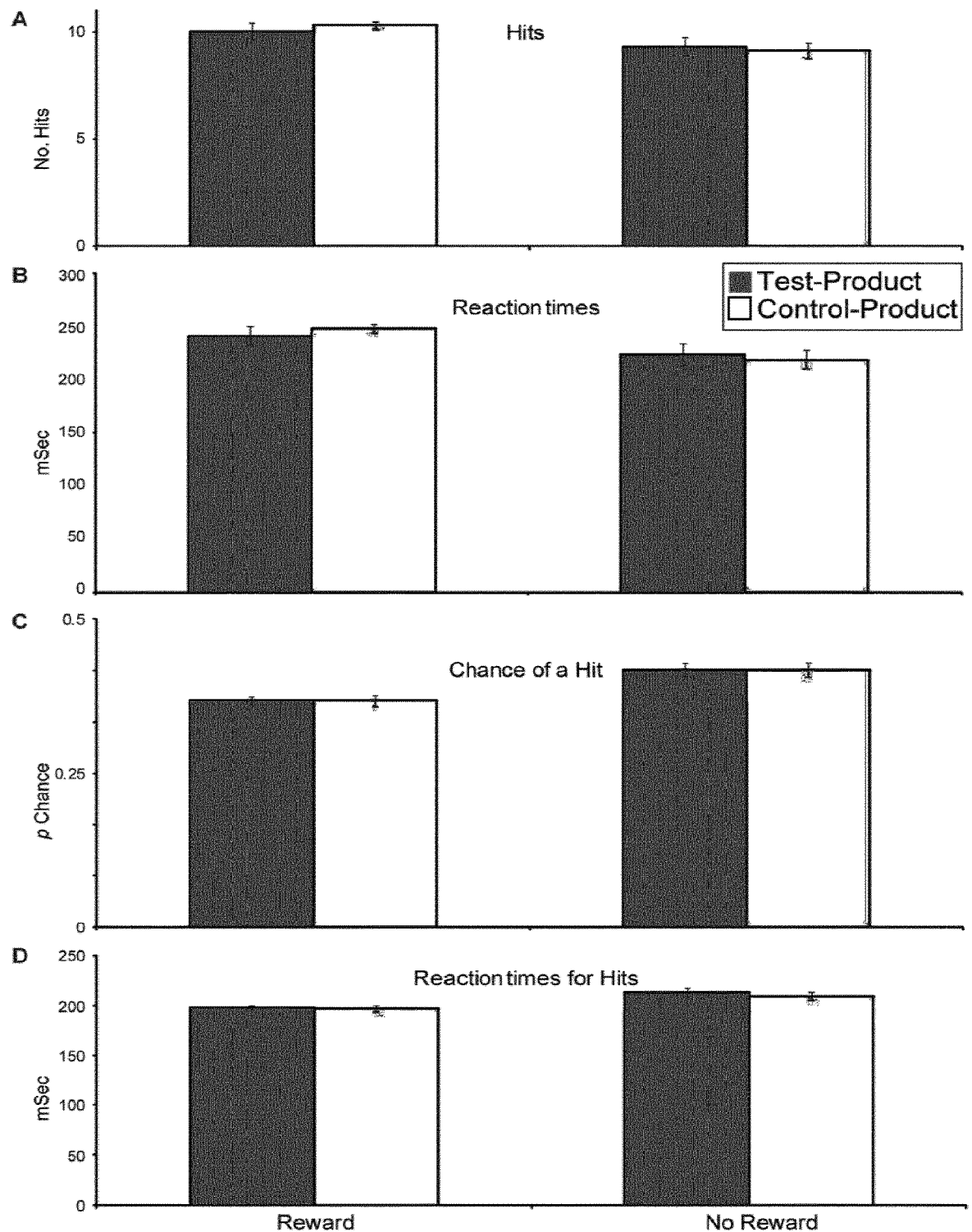
FIG. 4 shows behavioral results of the Reward processing task. Number of hits (A), Reaction times (B), probability of a response being correct (C), and reaction times for Hits only (D) are depicted for Reward and No Reward conditions. Comparing Test-Product (Left bars) to Control-Product (Right bars) revealed no effects of product consumption. Brain responses can, thus, not be attributed to behavioural differences.

Reward Processing:

The number of Hits for each condition (Reward, No Reward) was calculated per session for each subject (FIG. 4A). A Product (Test-Product, Control-Product)×Reward (Reward, No Reward)×2×2 repeated measure ANOVA revealed a main effect of Reward ($F_{1,27}$=19.822, P<0.001), with no other main effects or interactions.

The probability of a response being a Hit was calculated per session for each subject (FIG. 4C). A Product (Test-Product, Control-Product)×Reward (Reward, No Reward)× 2×2 repeated measure ANOVA revealed a main effect of Reward ($F_{1,27}$=19.822, P<0.001), with no other main effects or interactions.

Reaction times for each condition (Reward, No Reward) were averaged over each session for every subject for Hits only (FIG. 4D). A Product (Test-Product, Control-Product)× Reward (Reward, No Reward)×2×2 repeated measure ANOVA revealed a main effect of Reward (F1, 25=44.726, P<0.001), with no other main effects or interactions.

fMRI

Figure 5:
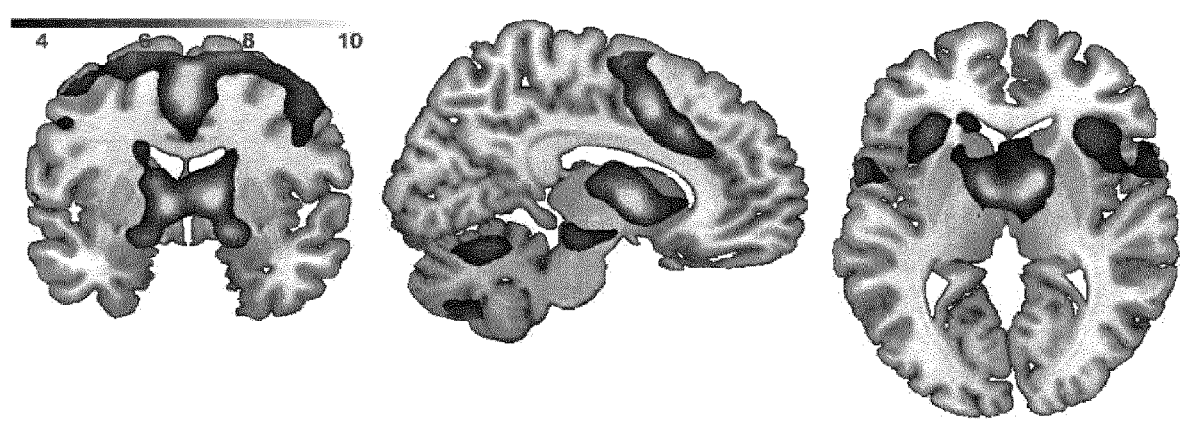
FIG. 5 shows that the reward anticipation was successful in probing the neural circuits involved in reward processing. These include the striatum, cingulate cortex, insula and motor cortex.

Reward Processing:

Comparing the Reward condition to the No-Reward condition revealed greater BOLD signal in regions commonly detected in reward anticipation studies (FIG. 5). These included striatal regions, middle cingulate cortex, supplementary motor areas and the middle frontal gyrus (Table 2).

TABLE 2

Results Main effect Reward task: Brodmann areas, MNI coordinates and Z-values for significant activations

| REWARD vs NO REWARD Foci of Activation | BA | MNI Coordinates X | Y | Z | Z value | Cluster size |
|---|---|---|---|---|---|---|
| R middle cingulate cortex | 24/32 | 4 | 22 | 36 | 7.59 | 8176 |
| R SMA | 6 | 6 | 8 | 52 | 7.47 | |
| R SMA | 6 | 2 | 0 | 62 | 6.93 | |
| R caudate nucleus | | 12 | 0 | 4 | 7.23 | 14290 |
| L caudate nucleus | | −8 | 2 | 0 | 7.11 | |
| L cerebellum | | −34 | −42 | −38 | 6.73 | |
| L middle frontal gyrus | 9 | −34 | 44 | 32 | 5.02 | 2.61 |
| R middle frontal gyrus | 9 | 38 | 48 | 28 | 4.98 | 456 |
| R middle frontal gyrus | 9 | 40 | 58 | 14 | 4.49 | |

Figure 6:
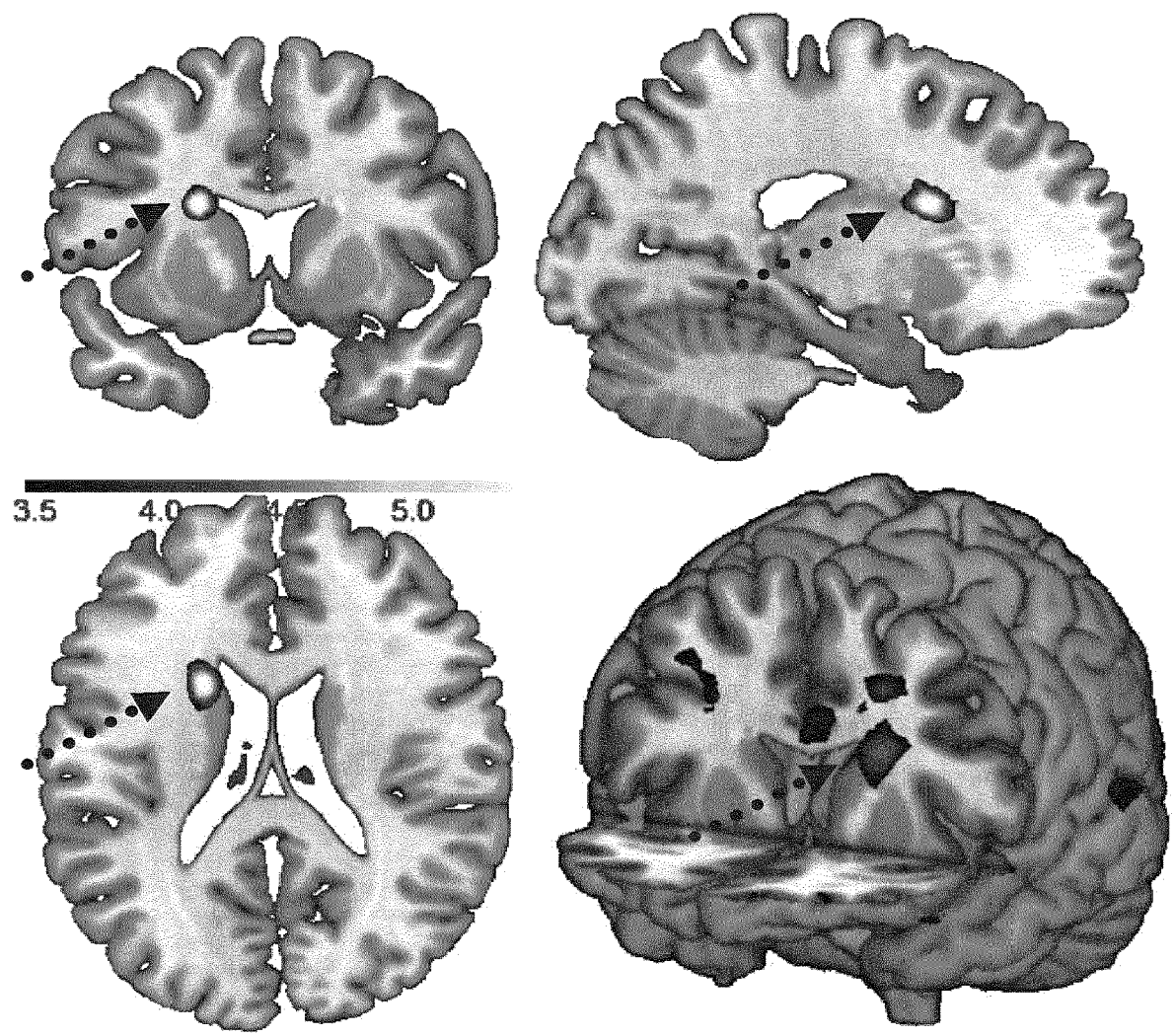
FIG. 6 shows that following Control Test-Product consumption, neural responses to Reward are highly induced in the dorsal caudate nucleus in comparison to after Test-Product consumption. This area has been implicated in higher cognitive processing integrating affective, motor and working memory components. (Area indicated by an arrow).

Significant at P < 0.05 FWE whole-brain cluster-level corrected
Cluster size in number of significant voxels at p < 0.001, uncorrected
All significant local maxima within 8 mm distance are reported Product Effects on Reward Processing (Control-Product Vs Test-Product (LumiVida)):

Testing for the influence of Product consumption on neural processing in the reward task we find greater BOLD signal during Reward anticipation compared to No-reward anticipating following Control-Product consumption (FIG. 6). This effect centers on the dorsal caudate nucleus (Table 3).

TABLE 3

Product effect on Reward task: Brodmann areas, MNI coordinates and Z-values for significant activations

| Control Product vs Test Product Foci of activation | BA | MINI Coordinates X | Y | Z | Z value | Cluster size |
|---|---|---|---|---|---|---|
| L caudate nucleus | | −20 | 10 | 22 | 4.86 | 143 |

Figure 7:
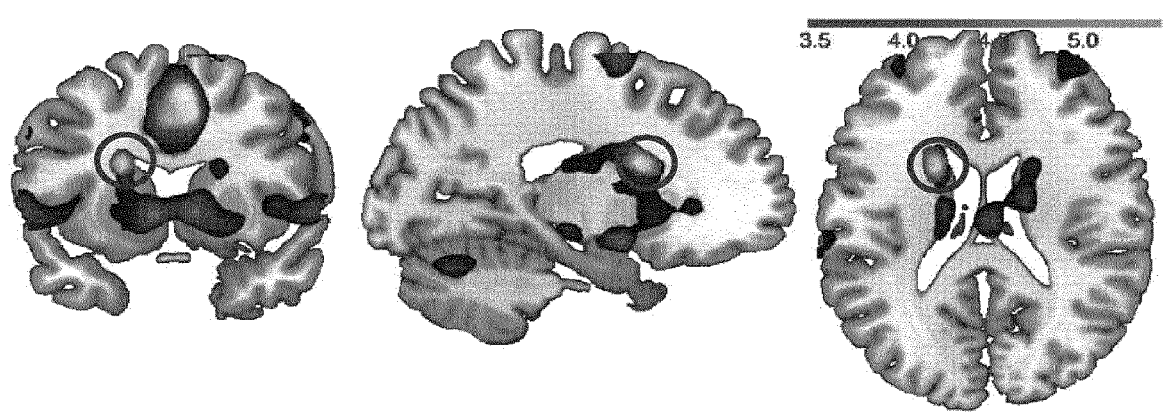
FIG. 7 shows the effect of Product consumption on neural processing of reward fall (indicated by a circle) within areas indicated by the main effect of reward processing.

Significant at P < 0.05 FWE whole-brain cluster-level corrected
Cluster size in number of significant voxels at p < 0.001, uncorrected
All significant local maxima within 8 mm distance are reported The region affected by product consumption is within those regions indicated in the main effect of reward anticipation (FIG. 7).

In conclusion, Test-Product consumption reduced neuronal processing differences between anticipation of reward and no reward.

We claim:

1. A method of assisting an animal in refraining from indulging in an undesired behavior and/or resisting from indulging in an addictive behavior by lessening reward anticipation which is derived from indulging in the behavior, wherein the method comprises the steps of:
   a) administering a hydrolyzed hen egg lysozyme composition which provides an effective daily dose of up to 800 mg tryptophan sufficient to lessen reward anticipation by the animal which is derived from indulging in an undesired behavior and/or an addictive behavior, wherein the composition comprises a ratio (Trp/LNAA) of tryptophan (Trp) to large neutral amino acids (LNAA) of between 0.15 and 0.20, and wherein the composition does not contain any free Trp and the Trp is only present in peptide-form, and
   b) noticing the animal refraining abstinence from and/or resisting indulging in the behavior.

2. The method according to claim 1 wherein the animal is a human.

3. The method according to claim 1 wherein the animal is an animal in a zoo, a farm animal, a pet or companion animal, or a racing animal.

4. The method according to claim 1 wherein the behavior is selected from the group consisting of smoking, alcohol abuse, gambling, drug abuse, compulsive behaviors, uncontrollable behaviors, cravings, and potentially harmful risky behaviors.

5. The method according to claim 1 wherein the behavior is a habit which the individual wishes to break.

6. The method according to claim 1 wherein the hydrolyzed lysozyme composition is present in a food, feed, nutraceutical, or food supplement.

7. The method according to claim 1 wherein the hydrolyzed lysozyme is an adjunctive treatment or supportive accompanying diet during dehabituation programs, or to assist dehabituation processes.

8. The method according to claim 1 wherein the behavior is selected from the group consisting of compulsive shopping, compulsive eating, hoarding, improper sexual behaviors, kleptomania, pyromania, cutting and self harm.

* * * * *